United States Patent [19]

Zografos

[11] Patent Number: 5,285,960
[45] Date of Patent: Feb. 15, 1994

[54] LITHIUM CHLORIDE HUMIDISTAT

[75] Inventor: Antonios I. Zografos, Oakland, Calif.

[73] Assignee: Gas Research Institute, Chicago, Ill.

[21] Appl. No.: 972,987

[22] Filed: Nov. 10, 1992

[51] Int. Cl.[5] .............................................. B01F 3/02
[52] U.S. Cl. ................................ 236/44 E; 73/335.05
[58] Field of Search ....................... 73/335.02, 335.05; 236/44 A, 44 R, 44 E

[56] References Cited

U.S. PATENT DOCUMENTS

| 1,459,391 | 6/1923 | Clausen | 73/335.02 X |
| 2,064,651 | 12/1936 | Fiene | 177/311 |
| 2,398,333 | 4/1946 | Shoemaker | 236/44 |
| 2,594,163 | 4/1952 | Hayworth | 73/29 |
| 2,629,253 | 2/1953 | Deaton | 73/29 |
| 4,276,128 | 6/1981 | Nishino et al. | 204/38 |

OTHER PUBLICATIONS

V. Brancu and I. Manolache, "Electronic hygrometers designed at the National Institute of Metrology-Bucharest", *Metrologia aplicata* vol. XXVII, nr. 2 (1980) pp. 74-77.

Primary Examiner—William E. Wayner
Attorney, Agent, or Firm—Lorusso & Loud

[57] ABSTRACT

A simple, relatively low cost wall mountable humidistat that continuously indicates the water vapor content of gas, most preferably air. The humidistat has a conductivity probe with electrodes extending into two interconnected vials containing lithium chloride solution. Moisture is absorbed by the solution from the humid ambient air whereby a change of the volume of the solution results and the level of humidity can be determined.

11 Claims, 1 Drawing Sheet

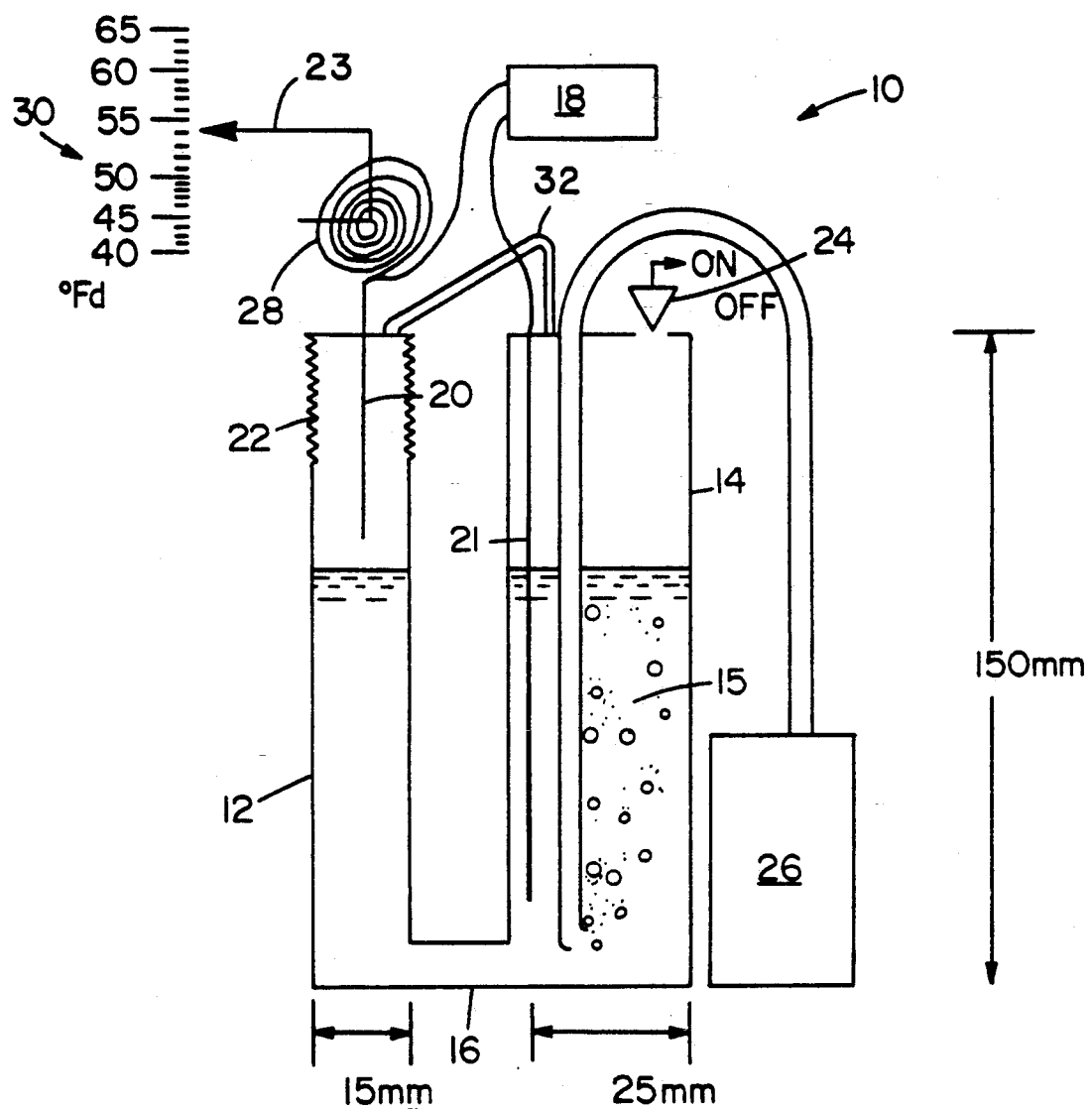

LITHIUM CHLORIDE HUMIDISTAT

BACKGROUND OF THE INVENTION

This invention relates to a humidity sensing apparatus employing lithium chloride solution whereby as moisture is transferred from the air to the solution, and the volume of the solution is increased, the level of humidity can be determined.

Measurement of humidity with high precision is still difficult compared with measurement of other physical variables of the atmosphere such as temperature and pressure. However, the need for easy and accurate measurement of humidity has increased in many fields such as food industries, agriculture, air conditioning and medical service, in order to control humidity, for humidifier or dehumidifier purposes.

Currently, there are several different types of apparatus to measure humidity. Electrical methods to measure humidity, where a change in humidity is detected by a change in electrical resistance as moisture is absorbed or desorbed by a deliquescent and/or hygroscopic substance, are widely known. However, apparatus employing these methods, i.e. those utilizing ionic conductivity, exhibit considerable drifting of the indications with passage of time by reason of polarization, eventually causing loss of calibration. Additionally, electrical indications are obtained from absorptions of various gaseous substances other than moisture. More importantly, such apparatus have not been fully satisfactory in their responsiveness, mode of hysteresis and the width of humidity range they can cover.

Another category of conventional electrical humidity sensors comprise a filament of an organic material such as human hair, nylon or polystyrene in combination with a strain gauge or microswitches so as to detect the deformation of the filament caused by absorption or desorption of moisture. These humidity sensors are traditionally unsatisfactory in their accuracy, responsiveness, hysteresis and heat resistance.

A still different type of conventional electrical humidity sensor utilizes swells of a synthetic resin containing fine particles of an electrically conductive material such as carbon or a metal but is characterized as being low in sensitivity, unsatisfactory in responsiveness and weak in high temperature.

Other sensors use a porous alumina layer to detect the change in humidity as a change either in electrical capacitance or impedance of the alumina layer resulting from absorption of moisture in the pores, or desorption therein. A drawback of this method is a considerable drifting of the dependence of the capacitance or the impedance on humidity with the passage of time.

While accurate measurements of humidity have been possible with apparatus utilizing the principle of ray absorption and transmission of wet and dry bulb hygrometers, these apparatus are considered too large scaled and costly to be of general use.

Thus, the humidity sensing devices now on the market all have certain drawbacks in their functional characteristics, resistance to environmental conditions, price, stability over a long period of time and/or convenience for usage and maintenance.

It is therefore an object of the present invention to provide a humidity sensing apparatus that is high in accuracy and sensitivity, and yet is small in size and low in cost.

It is another object of the present invention to provide a device that will continuously indicate accurately the water vapor content of gas, most preferably air.

A further object of the present invention is to provide a humidity sensing device that is capable of activating and deactivating a dehumidification device for complete atmospheric control of humidity.

SUMMARY OF THE INVENTION

The operation of the humidistat of the present invention is based on the absorption of water vapor by a salt solution, which, in turn, is determined by the chemical properties of the salt itself. Salts are extremely stable chemical compounds and thus problems of the prior art such as drifting of indication, loss of calibration, and hysteresis are eliminated. In particular, the prior art utilizes a film or solid block of the desired salt and does not disclose a humidistat utilizing a salt solution. The salt solution of the present invention overcomes the problems of the prior art. A further advantage of the present invention is the low cost of the humidistat.

The humidistat utilizes a conductivity probe with electrodes extending into two interconnected vials containing a lithium chloride solution. Absorption of water from humid ambient air by the solution causes a change in the level of solution in the vials. The change can be calibrated to determine the humidity level of the ambient air. Alternatively, the change in the level of the solution in the vials can be made to activate a switch to initiate or stop action of a dehumidifier (or humidifier) as the solution wets or ceases to wet one electrode of the conductivity probe. The humidistat of the present invention is wall mountable and relatively low cost.

The present invention will be better understood with reference to the following figure and detailed description of the invention.

BRIEF DESCRIPTION OF THE DRAWING

FIG. 1 is a schematic diagram of the wall mountable lithium chloride humidistat of the present invention in a dehumidifying mode.

DETAILED DESCRIPTION OF THE INVENTION

The lithium chloride humidistat 10 of the present invention includes two plastic vials, 12, 14 approximately 130–160 mm in length. The plastic vials 12 and 14 are connected at their bottoms through a connecting tube 16 and connected at their top portions through an interconnecting tube 32. Vial 12 is relatively smaller in diameter than vial 14. Preferably vial 12 is 10–20 mm in diameter and vial 14 is 20–30 mm in diameter The vials will contain a hygroscopic solution. While any hygroscopic solution such an sodium chloride, calcium chloride, calcium carbonate, sodium nitrite, sodium dichromate and potassium acetate, may be suitable for the present invention, with the goal of producing a low cost humidistat, it is preferable that a lithium chloride or lithium bromide solution be used for the present invention. Lithium chloride and lithium bromide are preferred due to their high affinity to water vapor, and extremely low absorption capacity for other gasses present in the atmosphere. The vials contain a dilute lithium chloride solution 15 having an initial concentration of approximately 23%.

The humidistat of the present invention includes a conductivity probe 18 including two electrodes 20, 21. The electrodes 20, 21 are permanently mounted in the vials 12, 14 from the top of the vial with the ground electrode 21 mounted in vial 14 and a second electrode 20 in vial 12. Ground electrode 21 extends into vial 14 into the lithium chloride solution 15 and second electrode 20 extends into vial 12 above the lithium chloride solution 15 contained therein. The top portion 22 of vial 12, however, is flexible so as to extend and retract. In this manner, electrode 20 can be immersed by means of a manually set positioner 23 at any level within the predetermined range desired for the purposes of this invention, as explained below.

The electrodes may be selected from, for example, platinum, titanium, palladium or graphite, although platinum is the preferred material for the electrodes 20, 21.

As stated above vials 12, 14 are closed when the humidistat is closed or at rest. Vial 14, however, has at its top, means 24 to open the vial 14, and thus open the humidistat system 10 to the ambient air. These means 24 can be valve means, and it is well within the knowledge of those skilled in the relevant art to develop a suitable means 24 to open the vial 14 to ambient air. When the humidistat is at the OFF position, the valve 24 will be closed and the system at rest with the lithium chloride solution 15 contained in the system 10.

When the valve 24 is open, the solution 15 adopts the temperature and humidity equilibrium of the ambient air. This process is enhanced by the continuous pumping of air to the bottom of vial 14 by air pump 26. The air pump 26 should be sized and selected according to the response time required for the system. Thus, if a faster response time is required, a more powerful pump will be desirable. While there may be some degree of agitation caused by the air flow in vial 14, it will be mitigated by the connecting tube 16, so that the liquid in vial 12 is not affected by agitation.

The two vials, 12, 14, of course, maintain the same level of the liquid solution 15. This is achieved by an interconnecting tube 32 which serves to equalize pressure over the headspace in the two vial levels allowing the two levels of liquid solution to rise and fall at the same instance.

As the humidity of the ambient increases, moisture will be absorbed by the solution 15 from the air until equilibrium is reached. In the process, the solution concentration reduces, and its volume due to the absorption of water. As the volume inc the level of solution 15 in the vials 12, 14 rises.

A calibration system 30 known to skilled in the relevant art, will translate the height of the position 23 to the relative humidity as determined from the height of the solution.

For example, at air temperature 80° F., a dew point (temperature at which air is saturated with moisture) change from 60° F. to 62° F., decreases the equilibrium concentration of the solution from 26.58% to 25.28%. For a system initially charged with 37.61 grams of 23% concentration lithium chloride solution, including vial 12, 150 mm long with a diameter of 15 mm and vial 14 at 150 mm long with a diameter of 25 mm, the volume of the solution 15 contained therein increases by approximately 1.67cm$^3$, and the corresponding level rise is 2.5 mm. Each level rise, compensated for temperature, is associated with a single ambient air humidity.

By appropriate positioning of the electrode 20 in vial 12, the electrode by means of the positioner 23 can be made to activate a switch for dehumidification when a set point is reached. As in the example above, since a 2.5 mm deflection can be easily detected, it is concluded that an accuracy of at least 2° F. dew point can be achieved easily. By inclining vial 12, the deflection can be magnified and accuracies of 1° F. or even higher may be possible.

In this scenario, once the dehumidification process commences, the air humidity reduces and moisture will be transferred from the solution 15 to the air. The solution 15 volume reduces and its level in the vials 12, 14 will drop. When the solution clears the electrode 20 in vial 12, the conductivity probe 18 turns the dehumidification switch off.

The equilibrium concentration changes with the temperature of the ambient air, and this change, for the limited range of normal indoor conditions, is almost linear. For a given humidity set point, the equilibrium concentration increases with increasing temperature. The electrode 20 in vial 12 is connected to a bimetallic spring 28, which is sized to correct the position of the electrode and compensate for non-standard temperatures.

The foregoing invention has been described with reference to its preferred embodiments. Although variations and modifications will occur to those skilled in the art, it is intended that such variations and modifications fall within the scope of the appended claims.

What is claimed is:

1. A wall mountable humidistat device comprising two vials connected at their bottoms through a connecting tube and containing a hygroscopic solution and a conductivity probe including a ground electrode and a second electrode, the ground electrode and the second electrode mounted in separate vials, means to admit ambient air to the solution in order to measure the humidity thereof;

and means responsive to the second probe being contacted by the solution to initiate a humidity control action 2. The wall mountable humidistat as set forth in claim 1 further comprising a bimetallic spring proximate said second electrode.

3. The wall mountable humidistat as set forth in claim 1 further comprising an air pump enabling the continuous pumping of air through the solution.

4. The wall mountable humidistat as set forth in claim 1 wherein one of said two vials has a flexible top portion which can be extended or retracted.

5. The wall mountable humidistat as set forth in claim 1 further comprising means for opening and closing the top portion of one of said vials.

6. The wall mountable humidistat as set forth in claim 1 including an interconnecting tube connecting one of said two vials to the other of said two vials at their top portions.

7. The wall mountable humidistat as set forth in claim 1 further comprising a calibration system for determining the height of said solution and therefore the desired ambient humidity.

8. The wall mountable humistat as set forth in claim 1 further comprising a switch to activate or deactivate the operation of a humidifier or a dehumidifier.

9. The wall mountable humidistat as set forth in claim 1 wherein:

one of said two vials includes said ground electrode;
the other of said two vials includes said second electrode;

the vial containing the ground electrode further comprising a tube connected to an air pump and a switch; and the vial containing the second electrode having a flexible top portion and further comprising a bimetallic spring and a calibration system proximate said second electrode.

10. The wall mountable humidistat as set forth in claim 1 wherein said hygroscopic solution is selected from the group consisting of lithium chloride, lithium bromide, sodium chloride, calcium chloride, calcium carbonate, sodium nitrite, sodium dichromate and potassium acetate.

11. A method for controlling humidity comprising:

providing a wall mountable humidistat including two vials connected at their bottoms through a connecting tube and their top portions through an interconnecting tube and containing a hygroscopic solution and a conductivity probe including a ground electrode and a second electrode, each mounted in separate vials;

providing a calibration system;

setting a desired humidity level on the calibration system;

exposing the humidistat to ambient air so that the hydroscopic solution will absorb or give off water;

causing a change in the level of solution in the vials;

calibrating to determine the humidity level of the ambient air; and activating a switch when said calibrating stop detects a certain level of solution so as to start the humidifying or dehumidifying process.

* * * * *

UNITED STATES PATENT AND TRADEMARK OFFICE
CERTIFICATE OF CORRECTION

PATENT NO. : 5,285,960
DATED : February 15, 1994
INVENTOR(S) : Zografos, Antonios L.

It is certified that error appears in the above-indentified patent and that said Letters Patent is hereby corrected as shown below:

Col. 3, line 46, after "volume" insert --increases,--;
line 47, after "volume" delete "inc" and insert --increases,--;
line 49, after "to" insert --those--; line 50, before "23" delete "position" and insert --positioner--; line 66, after "electrode" insert --20--;

Col. 4, line 34, after "vials" delete "," and insert --;--;
line 39, after "action" insert --.--; and Col. 6, line 15, after "start" delete "the" and insert --a--.

Signed and Sealed this

Thirteenth Day of September, 1994

Attest:

BRUCE LEHMAN

Attesting Officer  Commissioner of Patents and Trademarks